(12) United States Patent
Fedyna

(10) Patent No.: US 11,130,932 B2
(45) Date of Patent: Sep. 28, 2021

(54) BODY AND PET WASH ORGANIC FOAMING SOAP COMPOSITION AND DISPENSER

(71) Applicant: Got Green? LLC, Reading, PA (US)

(72) Inventor: Eileen E. Fedyna, Reading, PA (US)

(73) Assignee: Got Green? LLC, Reading, PA (US)

( * ) Notice: Subject to any disclaimer, the term of this patent is extended or adjusted under 35 U.S.C. 154(b) by 0 days.

(21) Appl. No.: 17/013,792

(22) Filed: Sep. 7, 2020

(65) Prior Publication Data

US 2020/0407666 A1    Dec. 31, 2020

Related U.S. Application Data

(63) Continuation-in-part of application No. 15/903,074, filed on Feb. 23, 2018, now Pat. No. 10,765,620.
(Continued)

(51) Int. Cl.
*A61K 8/00* (2006.01)
*C11D 9/38* (2006.01)
(Continued)

(52) U.S. Cl.
CPC .......... *C11D 9/38* (2013.01); *C11D 9/265* (2013.01); *C11D 17/08* (2013.01); *A47K 5/1201* (2013.01);
(Continued)

(58) Field of Classification Search
CPC .......... C11D 9/38; C11D 9/265; C11D 17/08; A61K 8/19; A61K 8/20; A61K 8/97; A61K 8/922; A61Q 19/10
See application file for complete search history.

(56) References Cited

U.S. PATENT DOCUMENTS 5,492,247 A    2/1996    Shu et al.
5,635,469 A    6/1997    Fowler et al.
(Continued)

OTHER PUBLICATIONS

AK Genena; H Hense; AS Junior; SM de Souza, "Rosemary (*Rosmarinus officinalis*)—a study of the composition, antioxidant and antimicrobial activities of extracts obtained with supercritical carbon dioxide", Food Science and Technology, Apr./Jun. 2008; 28(2): 463-469.
(Continued)

*Primary Examiner* — Necholus Ogden, Jr.
(74) *Attorney, Agent, or Firm* — Carrie Stroup

(57) ABSTRACT

An organic liquid and foaming soap composition and dispenser for use as a human hand, body wash and a pet wash, comprising: a) a foam-able organic liquid soap composition comprising the anti-microbial active ingredients of: organic shea butter; USDA approved natural spearmint oil; USDA approved natural lime oil; organic thyme oil; organic rosemary extract; and, b) a portable or fixed, manual or automatic foaming soap dispenser. The organic soap composition may further comprise a base soap comprising: saponified organic coconut oil; organic olive oil; organic sunflower oil; organic jojoba oil; organic aloe vera; and glycerin. And the organic soap composition has a shelf-life of about three years, and able to eradicate about 74.6% through 77.6% of the bacterial strain *Staphylococcus aureus* after at least one minute of direct contact with the composition. The dispenser is a fixed wall or sink mounted, or a portable bottle, including a mini-foaming leave-on sanitizer.

20 Claims, 11 Drawing Sheets

| DILUTION (VOLUME PLATED) | Test Organism: *Staphylococcus aureus* (ATCC 6538) | | | |
|---|---|---|---|---|
| | Exposure Time | | | |
| | 20 seconds | 1 minute | 2.5 minutes | 5 minutes |
| | Number of Survivors | | | |
| 10⁰ (1.00 mL) | T, T | T, T | T, T | T, T |
| 10⁰ (0.100 mL) | T, T | T, T | T, T | T, T |
| 10⁻¹ (0.100 mL) | T, T | 194, 202 | 160, 202 | 172, 178 |
| 10⁻² (0.100 mL) | 58, 37 | 27, 34 | 24, 18 | 20, 21 |
| 10⁻³ (0.100 mL) | 3, 5 | 9, 2 | 1, 2 | 0, 1 |

T = Too Numerous to Count (>300 colonies)

Related U.S. Application Data

(60) Provisional application No. 62/571,310, filed on Oct. 12, 2017.

(51) Int. Cl.
| | |
|---|---|
| *C11D 17/08* | (2006.01) |
| *C11D 9/26* | (2006.01) |
| *A47K 5/12* | (2006.01) |
| *A47K 5/16* | (2006.01) |
| *A61K 8/19* | (2006.01) |
| *A61K 8/20* | (2006.01) |
| *A61Q 19/10* | (2006.01) |

(52) U.S. Cl.
CPC ............... *A47K 5/1211* (2013.01); *A47K 5/16* (2013.01); *A47K 2201/02* (2013.01); *A61K 8/19* (2013.01); *A61K 8/20* (2013.01); *A61Q 19/10* (2013.01)

(56) References Cited

U.S. PATENT DOCUMENTS

| | | | |
|---|---|---|---|
| 6,068,162 | A | 5/2000 | De Winter et al. |
| 6,390,329 | B1 | 5/2002 | Maddox |
| 6,409,050 | B1 | 6/2002 | Ophardt et al. |
| 7,281,643 | B2 | 10/2007 | Lin |
| 7,838,477 | B2 | 11/2010 | Wenzel et al. |
| 8,091,739 | B2 | 1/2012 | Ophardt et al. |
| 8,113,388 | B2 | 2/2012 | Ophardt et al. |
| 8,308,027 | B2 | 11/2012 | Law et al. |
| 8,413,852 | B2 | 4/2013 | Ophardt et al. |
| 8,991,657 | B2 | 3/2015 | Ciavarella et al. |
| 9,439,841 | B2 | 9/2016 | Wegner et al. |
| 9,447,366 | B2 | 9/2016 | McCarthy et al. |
| 10,064,813 | B2 * | 9/2018 | Florence ................ A61K 8/375 |
| 2012/0288478 | A1 * | 11/2012 | Florence ................ A61K 8/064 424/93.1 |
| 2013/0119083 | A1 | 5/2013 | Ophardt et al. |
| 2015/0005215 | A1 | 1/2015 | McCarthy |
| 2015/0152359 | A1 | 6/2015 | McCarthy |
| 2017/0027390 | A1 | 2/2017 | Maercovich |
| 2019/0110978 | A1 | 4/2019 | Fedyna |

OTHER PUBLICATIONS

M Al-Hijazeen, M. Al-Rawashdehi, "Preservative effects of rosemary extract (*Rosmarinus officinalis* L.) on quality and storage stability of chicken meat patties", Food Sci. Technol, ahead of print Epub Nov. 13, 2017.

Y. Shahbazi, "Chemical Composition and In Vitro Antibacterial Activity of Mentha spicata Essential Oil against Common Food-Borne Pathogenic Bacteria", J Pathog. 2015; 1-5.

Y. Shahbazi, N. Karami, N. Shavisi, "Effect of Mentha spicata essential oil on chemical, microbial, and sensory properties of minced camel meat during refrigerated storage", Feb. 2018; 38(1): 1-7.

K. Sowndhararajan, S. Kim, "Influence of Fragrances on Human Psychophysiological Activity: With Special Reference to Human Electroencephalographic Response", Sci Pharm 2016; 84(4): 724-752.

S.S. Bhandari, M.P. Kabrab, "To evaluate anti-anxiety activity of thymol", Journal of Acute Disease, 2014, 3(2): 136-140.

CM Priestley, EM Williamson, KA Wafford, and DB Sattelle, "Thymol, a constituent of thyme essential oil, is a positive allosteric modulator of human GABAA receptors and a homo-oligomeric GABA receptor from *Drosophila melanogaster*", Br J Pharmacol. Dec. 2003; 140(8): 1363-1372.

T. Lockette, "Florida researchers use essential oil as earth-friendly pesticide", SouthEast FarmPress, Apr. 21, 2004.

EPA Red Facts, Thymol, EPA-738-F-93-010, Sep. 1993.

TM Nalawade, K Bhat, SHP Sogi, "Bactericidal activity of propylene glycol, glycerine, polyethylene glycol 400, and polyethylene glycol 1000 against selected microorganisms," J Int Soc Prev Community Dent. Mar.-Apr. 2015; 5(2): 114-119.

Office Action, U.S. Appl. No. 15/903,074, dated Aug. 21, 2019.

M.H. Taleb et al., "*Origanum vulgare* L. Essential Oil as a Potential Anti-Acne Topical Nanoemulsion—In Vitro and In Vivo Study", Molecules. Sep. 2018; 23(9): 2164.

T.H. Lee et al., "Protective effect of Thymol essential oil from Thynus quinquecostatus extracts on UV irradiation-induced skin aging by supressiong MMP-1 expression and collagen degradation", Federation of American Societies for Experimental Biology (FASEB), Abstract, vol. 32, Issue S1, Apr. 1, 2018.

"Tea 'controls female hair growth'", BBC News Online, Feb. 20, 2007.

M. T. Islam et al., "Anticancer Activity of Thymol: A Literature Based Review and Docking Study with Emphasis on its Anticancer Mechanisms", IUBMB Life, Oct. 11, 2018, pp. 9-19.

El-Shoraky and Shala, "Antifungal Activity of Spearmint and Peppermint Essential Oils against Macrophomina Root Rot of Cotton ", J. Plant Prot. and Path., Mansoura Univ., vol. 9 (11): 775-781, 2018.

Alves et al., "Unveiling the Antifungal Potential of Two Iberian Thyme Essential Oils: Effect on C. albicans Germ Tube and Preformed Biofilms", Front Pharmacol. 2019; 10:446.

L. Jing et al., "Antifungal Activity of Citrus Essential Oils", Journal of Agricultural and Food Chemistry, Mar. 2014, Abstract.

P. Mollarafie et al., "Antibacterial and wound healing properties of thymol (*Thymus vulgaris* Oil) and its application in a novel wound dressing", Journal of Medicinal Plants, Dec. 2015, 14(53):69-81, Abstract.

K. Alt, "Doggy Day Spa: Essential Oils For Dogs", Canine Journal Online, Oct. 18, 2019. https://www.caninejournal.com/essential-oils-for-dogs/.

P. Junquera, "Thymol, Natural Plant Insecticide for veterinary use in Dogs, Cats, Horses, Cattle, Sheep, Goats, Pigs & Poultry", Nov. 19, 2018. https://parasitipedia.net/index.php?option=com_content&view=article&id=3667&Itemid=4064.

"Best Antibacterial Dog Shampoos [2020] Medicated, Natural & Spray", Reviews Worthy. Downloaded Aug. 29, 2020. https://www.reviewsworthy.net/dogs/shampoo/why-use-antibacterial-dog-shampoos.

Grieves, "Natural Oils for Dogs That Can Help With Dog Skin Conditions", Pet MD, Dec. 11, 2018.

S.S. Bhandari et al., "To evaluate anti-anxiety activity of thymol", Journal of Acute Disease, vol. 3, Issue 2, 2014, pp. 136-140, Abstract.

G. Seaman,"8 Common Household Chemicals Harming your Pets, & their Non-Toxic Alternatives", Mar. 16, 2012 . https://learn.eartheasy.com/articles/8-common-household-chemicals-harming-your-pets-their-non-toxic-alternatives/.

* cited by examiner

| DILUTION (VOLUME PLATED) | Test Organism: *Staphylococcus aureus* (ATCC 6538) | | | |
|---|---|---|---|---|
| | Exposure Time | | | |
| | 20 seconds | 1 minute | 2.5 minutes | 5 minutes |
| | Number of Survivors | | | |
| 10° (1.00 mL) | T, T | T, T | T, T | T, T |
| 10° (0.100 mL) | T, T | T, T | T, T | T, T |
| 10⁻¹(0.100 mL) | T, T | 194, 202 | 160, 202 | 172, 178 |
| 10⁻²(0.100 mL) | 58, 37 | 27, 34 | 24, 18 | 20, 21 |
| 10⁻³(0.100 mL) | 3, 5 | 9, 2 | 1, 2 | 0, 1 |

T = Too Numerous to Count (>300 colonies)

FIG. 1

| Test Organism | Exposure Time | CFU/mL in Test Population Control ($Log_{10}$) | CFU/mL of Survivors | $Log_{10}$ Survivors | Percent Reduction | $Log_{10}$ Reduction |
|---|---|---|---|---|---|---|
| *Staphylococcus aureus* (ATCC 6538) | 20 seconds | 7.8 x 105 (5.89) | 4.8 x 10⁵ | 5.68 | 38.5% | 0.21 |
| | 1 minute | | 1.98 x 10⁵ | 5.30 | 74.6% | 0.59 |
| | 2.5 minutes | | 1.81 x 10⁵ | 5.26 | 76.8% | 0.63 |
| | 5 minutes | | 1.75 x 10⁵ | 5.24 | 77.6% | 0.65 |

FIG. 2

BODY AND PET WASH ORGANIC FOAMING
SOAP COMPOSITION AND DISPENSER

PRIORITY CLAIM

The present application claims the benefit of priority to U.S. Pat. No. 10,765,620 that issued on Sep. 8, 2020, which claim priority to U.S. Provisional Ser. No. 62/571,310, filed Oct. 12, 2017 by E. Fedyna, the entire contents of both of which are hereby incorporated by reference in the entirety.

TECHNICAL FIELD

The present disclosure generally relates to anti-microbial organic pet and body wash soaps, and in particular to environmentally friendly, anti-microbial, organic plant-based compositions for use in a recyclable portable foaming soap dispenser.

TRADEMARKS DISCLAIMER

The product names used in this document are for identification purposes only. All trademarks and registered trademarks are the property of their respective owners.

BACKGROUND

Wholly organic liquid human and pet body wash soap compositions are desirable because naturally occurring ingredients are more healthful to the human body when absorbed into the dermis and present no harmful or "toxic residual effect" within or around the bloodstream. Contrarily, non-organic, traditional soaps comprise chemicals that are harmful to both the user and the environment, such as: Triclosan, Sodium Lauryl Sulfate (SLS), Diethanolamine (DEA), Parabens, Synthetic Colors, Synthetic Fragrance, Urea, Propylene Glycol, 1,4-Dioxane, Ethyl Alcohol (Ethanol) and Benzalkonium Chloride (BAC).

Triclosan: In 2016, the Food and Drug Administration (FDA) issued a rule stating that over-the-counter consumer antiseptic wash products containing many potentially harmful antibacterial active ingredients—including triclosan and triclocarban—can no longer be marketed to consumers. These products include liquid, foam and gel hand soaps, bar soaps, and body washes. Research has shown that triclosan: alters hormone regulation in animals; contributes to the development of antibiotic-resistant germs; and is harmful to the immune system. The compositions of the present invention do not comprise triclosan, triclocarban, or any other non-organic, plant-based ingredient.

Environment: Organically derived ingredients provide not only an effective body washing experience, but also, provide a less toxic avenue for potential environmental hazards. Liquid soap compositions to date use harsh preservatives, such as formaldehyde, urea, parabens and sulfates like cocamidopropyl betaine, which can get into lakes and waterways and cause allergic reactions and derma irritation. Use of these harsh preservatives require drinking water processing facilities to remove them, resulting in more waste elimination work.

Soaps require preservatives to: help prevent microbial growth and rancidity in the soap, maintain its effectiveness, and increase the shelf-life of the soap. In the past, soap compositions have relied upon non-organic, chemical means of extending a soap's shelf-life because harm to the user from exposure to the chemical preservatives was not well known or understood, and because alternative non-chemical preservatives were ineffective or too costly.

For example, organic soaps have a shelf-life of 18 through 24 months, while commercial chemical soaps can be stored for up to 3 years. Additionally, Deb Soap™ and AntiBac FH Pure Foam™ chemical soap lasts up to 30 months, and castor oil-based soaps have a shelf life of approximately one-year time, and sunflower oil-based soaps have a shelf life of 3 to 6 months. When the product expires, the oils go rancid, change in odor and color (e.g. brown), become moldy and also tend to separate.

Pet Wash: Pets also require a body wash that is able to prevent and treat lice, fleas, flies, parasites, ticks, etc. The body wash is also non-allergenic and non-toxic to the pet (e.g. cats and dogs).

What is needed within the soap industry is an organic plant-based liquid or foaming soap for use as a human and pet body wash that does not comprise any non-organic chemical preservatives, but which has strong anti-microbial properties and a shelf-life that is equivalent to, or superior to, chemical soaps; and a wall mounted soap dispenser for use with the composition, wherein the dispenser and its refillable soap cartridge are environmentally friendly, e.g. made entirely from recyclable materials. The body wash should be effective against human and pet skin infections (e.g. prevent acne, anti-bacterial, anti-fungal, anti-parasite, etc.) while moisturizing and hydrating the skin and/or fur.

SUMMARY

Anti-Microbial Organic Foaming Soap Compositions

Liquid and foaming soap compositions according to the invention can be made wholly organic with a long shelf-life because of a newly-derived combination of organic ingredients processed in certain ways. These organic blends are highly preferable because they contain a synergistic combination of "naturally occurring antibacterial agents" in addition to vitamins and minerals known to protect the skin's surface.

The various embodiments of anti-microbial, foam-able composition of the present disclosure comprise the following anti-microbial active ingredients, all of which are oils certified to USDA Organic Standards: organic shea butter; organic or natural spearmint oil; USDA approved natural lime oil; organic thyme oil; and organic rosemary extract.

As used herein, the term "natural" refers to an ingredient that is approved under the USDA National Organic Program (7 CFR Part 205) that establishes specific provisions for the use of non-organic agricultural ingredients in processed products labeled "organic" or "made with organic (specified ingredients or food group(s))." Sections 205.105 (e)(f)(g) prohibit excluded methods, ionizing radiation and sewage sludge, as defined in 205.2. In an embodiment, "natural" means it is USDA non-organic certified for not being irradiated or exposed to chemicals of any kind.

In an embodiment of the organic soap composition, the organic shea butter is in a range from about 0.5 weight percent to about 5% weight percent.

In an embodiment of the organic soap composition, the organic or natural spearmint oil is in a range from about 0.50 weight percent to about 5.0 weight percent.

In an embodiment of the organic or natural soap composition, the United States Department of Agriculture (U.S.D.A) approved natural lime oil is in a range from about 0.4 weight % to about 5.0 weight %.

In an embodiment of the organic soap composition, the organic thyme oil is in a range from about 0.04 weight % to about 2.0 weight %.

In an embodiment of the organic soap composition, the organic rosemary extract is in a range from about 0.01 weight % to about 0.13 weight %.

In an embodiment, the composition further comprises a base soap composition of: saponified organic coconut oil; organic olive oil; organic sunflower oil; organic jojoba oil; organic aloe vera; and glycerin. In an embodiment, the composition may further comprise glycerin as a base soap ingredient, wherein the glycerin is a by-product of the manufacturing product from combining the organic essential oils with water and alkali, and then glycerin is added back into the composition.

Scented or Unscented Base Soap Composition: In an embodiment, the present disclosure comprises the base soap composition alone without the anti-microbial active ingredients, with or without at least one organic scented oil.

The compositions disclosed herein do not comprise sulfites, non-organic plant-based chemicals, or synthetic compounds. In an embodiment, the compositions are 100% organic; and another embodiment, the compositions are certified with organic ingredients, wherein all ingredients are organic, with the exception of the natural lime oil.

Formulations: the anti-microbial composition of the present disclosure is stored in a liquid formulation that based upon the type of soap dispenser may be dispensed as a liquid (e.g. pump dispenser) or a foam (foaming dispenser). In smaller quantities, the anti-microbial composition is left on the skin as a foamed or liquid "hand sanitizer" that is absorbed into the skin without leaving a sticky or tacky residue.

Shelf-life: the anti-microbial composition of the present disclosure has a shelf-life of about three years, which is equivalent to non-organic liquid and foaming soaps.

Anti-microbial: the compositions of the present disclosure exhibit anti-microbial properties.

Foaming Soap Dispenser

In an embodiment, the entire dispenser housing, and the refillable soap cartridge are made entirely of recyclable material, such as recyclable plastic material that comprises at least one of: polyethylene terephthalate (PET); high density polyethylene (HDPE); polyvinyl chloride; low density polyethylene (LDPE); polypropylene (PP); polystyrene (PS); and ABS In an embodiment the dispenser is a fixed dispenser, such as a wall mounted dispenser, or a sink mounted dispenser.

In an embodiment, the dispenser is portable (e.g. a bottle), and a top manually pump activated by pushing downward.

In all embodiments, the soap dispenser comprises markings to indicate that the soap is an environmentally friendly, organic plant-based, such as: a "got green?®" trademark; a Got Green® website address that lists the compositions' anti-microbial active ingredients; and/or one or more green or partially green colored leaves on the front of the dispenser.

Foam Producing Soap Product

In an embodiment, of the present disclosure comprises a foam producing soap product comprising: a) a foam-able organic liquid soap composition comprising the anti-microbial active ingredients of: organic shea butter; USDA approved natural spearmint oil; USDA approved natural lime oil; organic thyme oil; and organic rosemary extract; b) a foam soap dispenser for dispensing the organic liquid soap composition as a premeasured amount of foaming soap, wherein the foam dispenser comprises: a recyclable plastic; a portable bottle with a manual top downward pump and a front label indicating the composition is an organic soap; and c) wherein the soap is able to be effectively used as a pet and/or human body wash to prevent and/or treat infections while moisturizing the hair and skin.

In an embodiment of the foam producing soap product, the foam soap dispenser is a portable manual soap dispenser, and comprises a top downward pushed manually operable pumping means.

In an embodiment of the foam producing soap product, the foam soap dispenser further comprises a liquid soap filled reservoir that is operatively connected to the pumping means for supplying the organic soap composition to the dispenser via a vertically mounted tube extending between the reservoir and a dispenser nozzle connected to a close/open valve.

In an embodiment of the foam producing soap product, the organic soap composition further comprises the base soap composition ingredients of: saponified organic coconut oil; organic olive oil; organic sunflower oil; organic jojoba oil; and organic aloe vera.

In an embodiment of the foam producing soap product, the organic soap composition further comprises glycerin that is produced during the process of making the base soap composition, that is remixed into the composition. In an embodiment of the foam producing soap product, the shelf-life of the organic soap composition is about three years.

In an embodiment of the foam producing soap product, the organic soap composition is able to eradicate about 74.6% through 77.6% of the bacterial strain *Staphylococcus aureus* after at least one minute of direct contact with the composition.

In an embodiment, the foam producing soap product is useable to clean and disinfect pet toys and bowls.

BRIEF DESCRIPTION OF THE DRAWINGS

FIG. 1 is a table of experimental results demonstrating that the maximum eradication of the bacteria *Staphylococcus aureus* (ATCC 6538) occurred with exposure between one minute and five minutes of the composition of Table 1 to the bacterial culture of Table 2, and wherein the dilution of bacteria is in the amount of at least $10^{-1}$ (0.100 mL) to $10^{-3}$ (0.100 mL).

FIG. 2 is a table of experimental results demonstrating that exposure of the composition of Table 1 to the bacterial culture of Table 2 for at least one minute resulted in 74.6% through 77.6% eradication of all of the bacterial colony forming units within the culture.

DETAILED DESCRIPTION OF EXEMPLARY EMBODIMENTS

Figure 3:
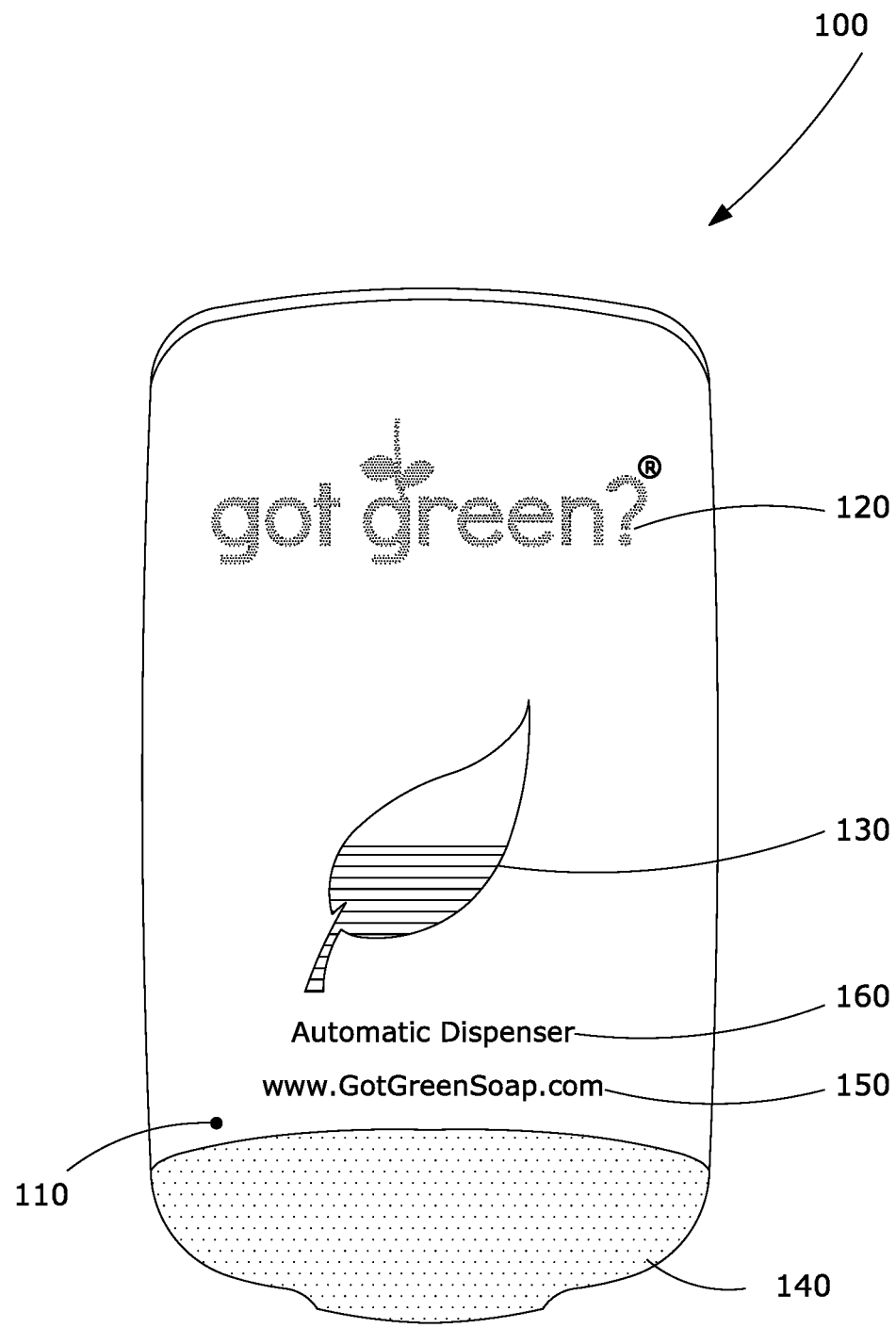
FIG. 3 is a front elevational view of an exemplary automatic foaming soap dispenser of the present disclosure.

A detailed description of a preferred embodiment and process is provided herein. It is to be understood, however, that the invention may be embodied in various forms and processed using other methods. Therefore, specific details disclosed herein are not to be interpreted as limiting, but rather as a basis for patent claims and as a representative basis for teaching one skilled in the art to employ the present invention in virtually any appropriately detailed system, structure or manner.

As used herein, the term "essential oil" refers to an essential oil as a product made by distillation with either water or steam or by mechanical processing of citrus rinds or by dry distillation of natural materials. Following the distillation, the essential oil is physically separated from the water phase. For an essential oil to be a true essential oil, it must be isolated by physical means only. The physical methods used are distillation (steam, steam/water and water) or expression (also known as cold pressing, a unique feature for citrus peel oils). There is one other method of oil isolation specific to a very limited number of essential oil plants. This is a maceration/distillation. In the process, the plant material is macerated in warm water to release the enzyme-bound essential oil.

As used herein, the term "by weight" or "wt. %" refers to the amount of the stated composition ingredient as a percentage of the entire composition: base soap ingredients (Table 2), or base soap ingredients plus scented essential oils, or base soap ingredients plus anti-microbial active ingredients (Table 1). For example, if the entire foaming soap composition disclosed herein has by weight 100 grams, then the composition comprises, in an embodiment, organic rosemary extract from 0.01 grams to 0.1 grams.

Wholly organic liquid hand soap compositions according to the invention are the first "organically formulated" hand soaps to be crafted without the use of chemically altered, man-made preservation methods. The natural preservation methods described herein extend the duration of shelf life beyond that of what many inorganic preservatives can achieve. These compositions maintain stability with use the of rosemary organic extract and the process used to incorporate it into the compositions.

In accordance with 7 CFR § 205.301, the soap compositions of the present disclosure are "made with organic", which contains (by weight, excluding water and salt) at least 70 percent to 94 percent organically produced ingredients. The soap compositions of the present disclosure are also certified to USDA Organic Standards.

As used herein, the term "anti-microbial active" and "active" are used interchangeably herein and refers to the soap composition ingredients that act in an unexpected synergistic manner (e.g. Table 1 ingredients) to render the soap composition able to reduce at least one type of bacterial infection or presence on the user's skin, such as a gram positive bacterial infection.

It is important to note in this context there is a distinction between pure rosemary essential oil and that of rosemary extract as a plant extract. Liquid that is distilled or separated from plant extract is commonly referred to as the "plant essence" and the minimal amount of "volatile liquid" left behind is the essential oil. Rosemary extract specifically is very different from "rosemary essential oil," as the extract has a very high level of antioxidants when absorbed or ingested. Antioxidants are known to fight "free-radicals"; therefore, when the extract is used as a method of preservation, it prevents the breakdown of natural products such as the wholly organic liquid hand soap compositions described herein. Rosemary oil, on the other hand, is used for a variety of medicinal purposes and does not contain the preservation level of an "extract" (e.g. see List of References infra (1, 2)).

The rosemary extract is added to the blended oils prior to the soap composition being mixed and created. This process results in doubling shelf-life by using the antioxidant properties of the rosemary extract to slow the breakdown of the other natural ingredients in the soap composition.

One preferred liquid hand soap composition according to the invention contains organic thyme oil, spearmint oil, and rosemary extract; and USDA approved natural lime oil; and shea butter.

Thymol wards off gram-positive bacteria on the skin's surface. This particular anti-microbial active oil also aids to create a residual barrier of protection on the hand's surface to prevent the spread of germs and parasitic matter, such as scabies and lice, from one person to another. Thyme essential oil also contains naturally occurring antibacterial properties that help prevent bacteria build-up in the sink drain by coating the metal pipe on the way down. In the future, this aspect will help prevent bacterial C. Duff sewage back-up, which is a current phenomenon occurring in hospital wash sinks.

Spearmint oil, certified to USDA Organic Standards, is used to mask the scent of thymol used in the composition, and provides an energized "uplifting" aroma. Spearmint also has natural antiseptic properties (due to the presence of menthol, myrcene and caryophyllene) that are effective against bacteria (3, 4). Additionally, both thymol and spearmint have been studied scientifically to stimulate the nerves and brain function, which is beneficial for users. A main factorial of this is thymol's ability to have an instant effect on brain activity, which has been revealed by monitoring brain activity via electroencephalograms. The mood encouraging nature of the composition is also being explored (5, 6, 7).

USDA approved natural lime oil is used to create a pleasing "spearmint-lime" scent. This also provides a novel twist on the scent. Just like the previously mentioned organic oils, lime oil also contains antiseptic, antiviral and antibacterial properties. A spearmint-lime scent appeals to both fans of citrus and of mint. Due to the natural "spearmint-lime" scent, which disperses in the air with the foaming dispenser disclosed herein, other air fresheners are not required. Additional organic plant-based scents may be added to the composition. And, the composition may be scented, or unscented.

Shea butter is used as a moisturizer, which helps the skin retain moisture after hand washing, but when utilized minimally as a "leave-on", helps transport the formula into the deeper layers of the derma and turn the once "wet" formula into a soft, silky feel after several minutes time. Additionally, due to the shea butter's cinnamic acid, it works as an anti-inflammatory and is found to reduce skin inflammation. Thus, the compositions of the present disclosure can be used to relieve the "aches and pains" symptoms of disorders and conditions, such as carpal tunnel syndrome and rheumatoid arthritis, by inducing a natural anti-inflammatory effect. Some previous and soap compositions comprise pharmaceutically-produced non-steroidal anti-inflammatory drugs (NSAIDS) that are used as the inorganic means for anti-inflammatory properties listed in the compositional makeup. This is not only dangerous, but due to the fact that a large amount of pharmaceutically produced NSAIDS contain formaldehyde and/or, this raises the risk of increased "premature" illness rates, e.g. nausea, headaches, respiratory problems and cancer (see U.S. Pat. No. 5,635,469 A that issued to TJ Fowler on Jun. 3, 1997).

Glycerin: in additional embodiments of the present disclosure, glycerin, which is a by-product of the manufacturing process using plant oils, is added back-into the final soap composition to produce a milder hand soap with enhanced moisturizing effect. Glycerin is a humectant, meaning that it attracts water. When glycerin is applied to the skin as an optional ingredient of the composition, it seals in moisture that might otherwise escape. Glycerin may also contribute to the anti-microbial activity of the soap composition (10).

Anti-bacterial Active Ingredients: A preferred version of the composition comprises the following combination of anti-microbial active ingredients: organic shea butter; USDA approved as natural spearmint oil; USDA approved as natural lime oil; organic thyme oil; organic rosemary extract; and glycerin. In another embodiment, glycerin is an additional ingredient.

The various compositions of the present disclosure exhibit strong, anti-microbial effects due to the unexpected synergistic effects of combining the ingredients of Table 1, which alone have some anti-microbial properties.

In an embodiment, the organic shea butter is in a range from about 0.5% (by weight) to about 5% (by weight).

In an embodiment, the natural spearmint oil is in a range from about 0.50 wt. % to about 5.0 wt. %. In an embodiment, the spearmint is natural-meaning it is USDA non-organic certified for not being irradiated or exposed to chemicals of any kind, (e.g. in the soil). In another embodiment, the spearmint is organic.

In an embodiment, the USDA approved natural lime oil is in a range from about 0.40 wt. % to about 5.0 wt. %.

In an embodiment, the organic thyme oil is in a range from about 0.04 wt. % to about 2.0 wt. %.

In an embodiment, the organic rosemary extract is in a range from about 0.01 wt. % to about 0.13 wt. %.

Table 1 provides a list of the weight percent range for each anti-microbial active ingredient within one exemplary foaming soap composition that is a preferred embodiment.

TABLE 1

| Antimicrobial Active Ingredients | Exemplary Range of Weight Percent |
|---|---|
| Organic Shea Butter | about 0.50 wt. % to about 5.0 wt. % |
| Natural Spearmint Oil | about 0.50 wt. % to about 5.0 wt. % |
| Natural Lime Oil | about 0.40 wt. % to about 5.0 wt. % |
| Organic Thyme Oil | about 0.04 wt. % to about 2.0 wt. % |
| Organic Rosemary Extract | about 0.01 wt. % to about 0.13 wt. % |

Base Soap Ingredients: the remainder of the foaming soap composition of the various embodiments of the present disclosure further comprises other organic oils, such as: saponified organic coconut oil; organic olive oil; organic sunflower oil; organic jojoba oil; and organic aloe vera (see Table 2). In an embodiment, the total of the base soap ingredients comprises at least about one of the following: 55%, or 60%, or 65%, or 70%, or 75%, or 80%, or 85% of the total composition. In another embodiment, the total base soap is about 89% of the total composition.

Due to the anti-microbial properties of the composition of Table 1, it can also be used as a leave on hand sanitizer when dispensed in smaller doses, wherein the composition is absorbed into the skin without leaving a sticky residue on the user's skin.

Unscented Versus Scented Soap

The various soap compositions of the present disclosure comprise the base soap ingredients of Table 2, which is an unscented version of the soap composition.

TABLE 2

| Base Soap Ingredients | Exemplary Range of Weight Percent |
|---|---|
| Saponified Organic Coconut Oil | about 50.0 wt. % to about 79.60 wt. % |
| Saponified Organic Olive Oil | about 1.0 wt. % to about 3.4 wt. % |
| Saponified Organic Sunflower Oil | about 1.0 wt. % to about 5.0 wt. % |
| Saponified Organic Jojoba Oil | about 0.20 wt. % to about 3.0 wt. % |
| Organic *Aloe Vera* | about .001 wt. % to about 0.20 wt. % |
| Glycerin | about 1.0 wt. % to about 5.0 wt. % |

Scented soap: The soap composition of the present disclosure may further comprise at least one of the following oils, or any combination thereof, to scent the soap: orange essential oil, lemon essential oil, lime essential oil, citrus blend essential oil, kiwi oil, strawberry essential oil, raspberry essential oil, elderberry essential oil, juniper berry essential oil, cranberry essential oil, pomegranate essential oil, vanilla essential oil, lemongrass essential oil, rosemary essential oil, patchouli essential oil, thyme essential oil, spearmint essential oil, peppermint essential oil, wintergreen essential oil, cinnamon bark and leaf essential oil, sage essential oil, basil essential oil, sweet basil essential oil, pine blend essential oil, frankincense essential oil, ginger essential oil, mandarin essential oil, tangerine essential oil, grapefruit essential oil, floral fragrance, lavender essential oil, rose essential oil, *gardenia* essential oil, geranium essential oil, sweet marjoram oil, nutmeg essential oil, bergamot essential oil, cardamom essential oil, chocolate fragrance oil, benzoin essential oil, and coconut fragrance oil.

Method of Making the Foaming Organic Soap

The organic liquid and/or foaming hand soap compositions according to the various embodiments of the present disclosure are made according to the following exemplary method.

Base Soap: The process begins with pre-mixing the rosemary extract with the non-anti-microbial active oils prior to its addition into the whole soap composition. In an embodiment, the base soap composition of Table 2 is utilized to make the unscented soap (one embodiment), to which at least one scented oil may be added (second embodiment), or to which the naturally occurring anti-bacterial ingredients of Table 1 are added (third embodiment).

For all embodiments, the rosemary extract and the base soap ingredients of Table 2, such as coconut and other plant-based oils (i.e. saponified organic coconut oil; organic olive oil; organic sunflower oil; organic jojoba oil; and organic aloe vera) are pumped into kettles. Then fluids (i.e. water at about 81 wt. %) are combined along with alkali (e.g. potassium hydroxide at about 3.48 wt. %) into the kettles. Following this, the certified base soap ingredients comprising the organic oils of Table 2, water and alkali combine to form liquid soap and glycerin. To create a "milder" soap, the glycerin is added back into the composition. This differs largely from generic, chemically-created liquid hand soap because they do not add the glycerin back into the finalized product during production. Failing to take this extra step results in a harsh hand soap formulation that can be very drying and irritating to skin.

After the cooking process has completed (e.g. duration of heating about 4 to 5 hours up to 200 degrees Fahrenheit), the base soap composition (with glycerin, or with the glycerin removed) is then pumped into tanks and cooled. The anti-microbial active organic oil ingredients (e.g. see Table 1 for exemplary weight percent amounts of each anti-microbial active ingredient) are then added into to the base soap composition, which creates the natural effect of the antiseptic and preserving properties in the hand soap Formulations and Methods of Use Formulations: the anti-microbial compositions of the present disclosure are stored in a liquid formulation that based upon the type of soap dispenser may be dispensed as a liquid or a foaming dispenser. In the portable mini-bottle of FIG. 12, the composition can be left on the user's skin as a sanitizer without leaving a sticky or tacky residue after being absorbed.

The compositions of the present disclosure are primarily used to reduce the amount and proliferation of pathogens: microbes, germs, parasites, viruses, fungi, ticks, bacteria, etc. on the user's hands, although all skin epidermis can also be sterilized.

In an embodiment, the compositions of the present disclosure should not cause user immune response resistance to pathogens, e.g. bacterial, viral, etc.

The compositions of the present disclosure can also be used as an anti-inflammatory and a topical analgesic due to the shea butter's cinnamic acid.

The compositions of the present disclosure can also be used to moisturize and deeply condition dry skin due to the shea butter.

The compositions of the present disclosure can also be used as a room air freshener because the plant oils in the anti-microbial active ingredients eradicate the airborne bacteria.

The compositions of the present disclosure can also be used as a bug repellent, such as to deter mosquitoes and ticks due to the thyme oil (8,9).

The compositions of the present disclosure can be used as a human body wash (e.g. for the shower or bath), and as a pet wash.

Experimental Data Demonstrating Anti-Microbial Activity

The anti-microbial properties of the composition of Table 1 were tested against the bacterial strain *Staphylococcus aureus*, with the American Type Culture Collection identifier (ATCC 6538).

Experimental Design: a suspension of the test organism *Staphylococcus aureus* (ATCC 6538) was exposed to the test substance of the composition of Table 1 for the specified exposure times. After exposure, an aliquot of the suspension was transferred to neutralizer (D/E Neutralizing Broth) and was assayed for survivors. Appropriate culture purity, neutralizer sterility, test population, and neutralization confirmation controls were performed.

Results: As illustrated in FIGS. 1 and 2, GOT GREEN SOAP (Batch # OR-73231) ready to use, demonstrated a 38.5% (0.21 $\log_{10}$) reduction of *Staphylococcus aureus* (ATCC 6538) survivors following a 20 second exposure time, a 74.6% (0.59 log 10) reduction of *Staphylococcus aureus* (ATCC 6538) survivors after a 1 minute exposure time, a 76.8% (0.63 $\log_{10}$) reduction of *Staphylococcus aureus* (ATCC 6538) survivors after a 2.5 minute exposure time and a 77.6% (0.65 $\log_{10}$) reduction of *Staphylococcus aureus* (ATCC 6538) survivors after a 5 minute exposure when tested at ambient temperature (20° C.).

Per FIG. 1, the maximum eradication of the bacteria *Staphylococcus aureus* (ATCC 6538) occurred with exposure of the composition of Table 1 to bacterial culture of Table 2, wherein the dilution of bacteria is in the amount of 0.001 bacteria colonies per 0.100 milliliters of the bacterial culture.

TABLE 3

| Test Organism | ATCC # | Growth Medium | Incubation Parameters |
| --- | --- | --- | --- |
| *Staphylococcus aureus* | 6538 | Tryptic Soy Agar + 5% Sheep Blood | 35-37° C., aerobic |

And as illustrated in FIG. 2, exposure of the composition of Table 1 to the bacterial culture of Table 3 for at least one minute resulted in 74.6% through 77.6% eradication of all of the bacterial colony forming units within the culture.

Shelf-Life Extended

Normally, organic liquid soaps have a short shelf-life of about one year because of the lack of a preservative. A sunflower oil-based liquid soap has an even shorter shelf-life of about 3-6 months. Chemical liquid hand soaps with artificial preserving agents have a shelf-life of about two years. Yet, the anti-microbial compositions of the present disclosure have a shelf-life of about three years, which is due in part to the unexpected synergistic effect of the combination of the oils of Table 1 for preserving the soap composition, especially the rosemary extract.

The organic rosemary extract is added to the base soap composition of Table 2 prior to the base soap composition being mixed, heated, and cooled. This process results in doubling shelf-life by using the antioxidant properties of the rosemary extract to slow the breakdown of the other natural ingredients in the soap composition.

Foam Producing Soap Product

The present disclosure further comprises a foam producing soap product comprising: a) a foam-able organic liquid soap composition comprising the anti-microbial active ingredients of Table 1: organic shea butter; USDA approved natural spearmint oil; USDA approved natural lime oil; organic thyme oil; and organic rosemary extract; and, b) a foam soap dispenser for dispensing the organic liquid soap composition as a premeasured amount of foaming soap, wherein the foam dispenser comprises: a recyclable plastic; a bottom front tab comprising a green color and a front label indicating the composition is an organic soap. The foam-able organic liquid soap composition further comprises the base soap composition of Table 2.

In another embodiment, the foaming soap composition comprises the base soap composition of Table 2, and with or without the addition of at least one scented oil; and without all of the oils of Table 1.

Cost Effective: The foam producing soap product of FIGS. 3-5 with the composition of Table 1 has been demonstrated to be more cost effective than commercial chemical soaps, due to the amount of soap dispensed with each pump, the higher viscosity and the longer shelf-life of the organic soap, and the volume of the results in significant cost savings. Table 4 comprising a study conducted in the King of Prussia (KOP) Mall comparing use of GOJO™ Foam Hand wash (Type: Antibacterial) to the present disclosure's Got Green? soap. Results: GOJO dispensers lasted about one week in public restrooms, whereas Got Green? dispensers lasted for about 3 weeks in the woman's restroom and about 1 month in the men's restroom. These was thus a $11.37 savings using Got Green? per case (case equals 4 fills) versus GOJO™

TABLE 4

| Company | No. of Fills | Price | Milliliters | Time Factor | Overall Cost |
|---------|--------------|-------|-------------|-------------|--------------|
| GOJO ™ | 1 | $12.85 | 1,250 | 1.0 | $10.28 |
| Got Green? ® | 1 | $22.31 | 1,000 | 3.0 | $ 7.44 |

Liquid and Foaming Soap Dispensers

The soap compositions for the present disclosure are housed in a soap dispenser that pumps out the soap in a liquid form, or as a foam, based upon the mechanical components of the dispenser.

The dispensers of the present disclosure are also either automatic, so that the user does not need to touch the dispenser (e.g. FIG. 3), or manual (e.g. FIGS. 4-12), where the user pushes inward on a bottom green colored tab.

In all embodiments of the present disclosure, the soap composition is housed within a dispenser that comprises markings to indicate that the soap is an environmentally friendly, organic plant-based soap, such as: a "got green?®" trademark 120 (Registration No. 4904158, issued on Feb. 23, 2016), with a green color of pantone shade 2427 C; and a green colored lower push-tab 140-146 on the bottom front of the dispenser. The push-tab in all embodiments is colored green per the dispenser color mark registration of FIGS. 6-9, 146, with the color mark application number 87457091, filed on May 19, 2017 by Fedyna, which claims pantone green color 2424 XGC, or 2424.

The front of the soap dispenser may further comprise a leaf-shaped clear or opaque window that displays the level of the soap composition remaining within the dispenser (e.g. FIGS. 3-5, 130).

The front of the soap dispenser may further comprise the Got Green® website address 150 that lists, for example, the composition's anti-microbial active ingredients, as well as, the intellectual property protection of the composition. The website may further list the intellectual property protection of the dispenser of FIGS. 3-6, such as design patent numbers. And the dispensers may have markings indicating the soap composition is "Plant-Based Foam Soap" as illustrated in FIG. 4, 163; or markings of "Plant-Based Foam Hand Soap", as illustrated in FIGS. 6-9, 162. Other decorative markings may also be added to the dispenser, such as a colored border on the front of the dispenser (e.g. FIG. 4, gold border 170).

Figure 4:
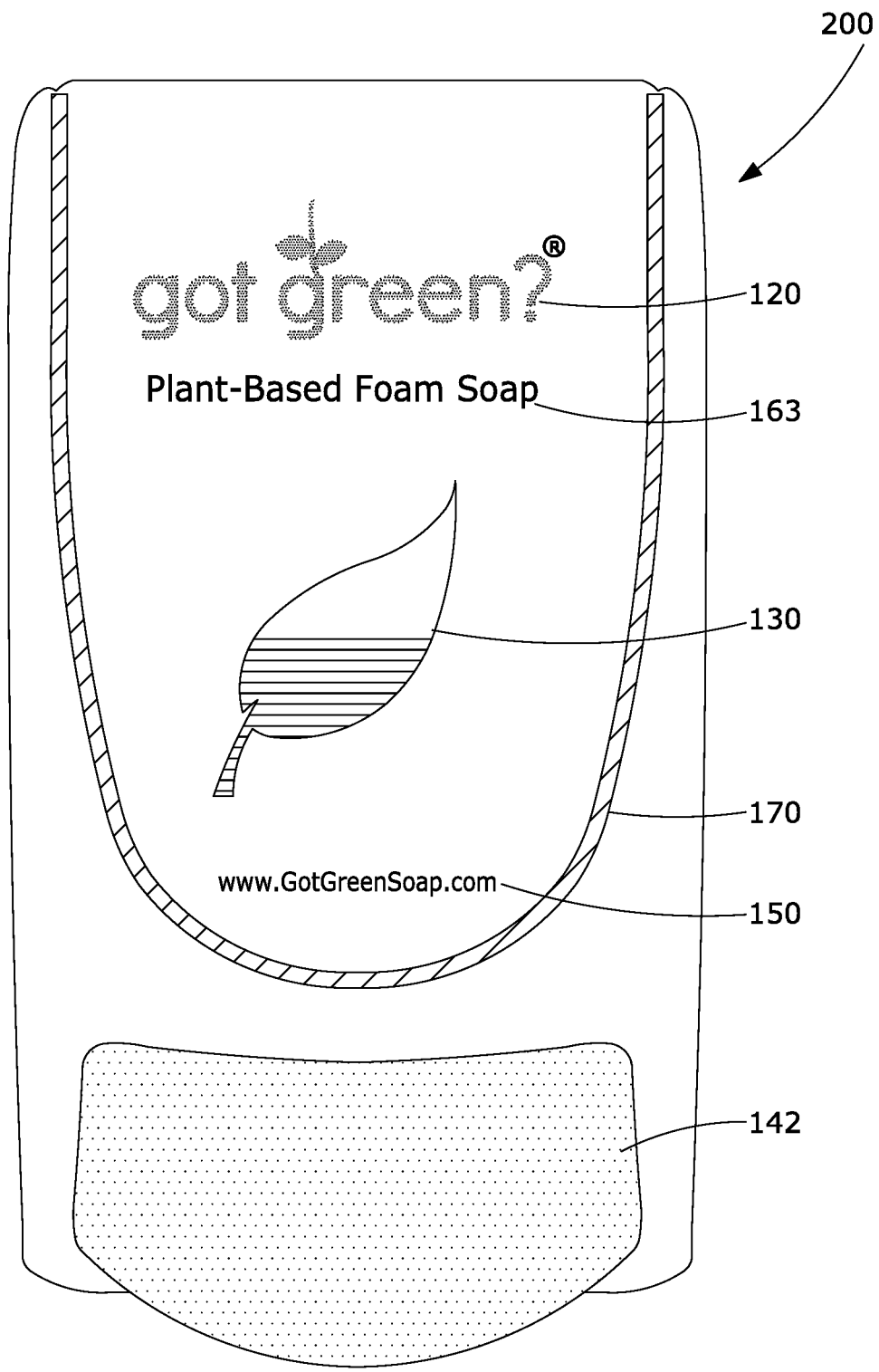
FIG. 4 is a front elevation view of an exemplary manual foaming soap dispenser of the present disclosure.
Figure 5:
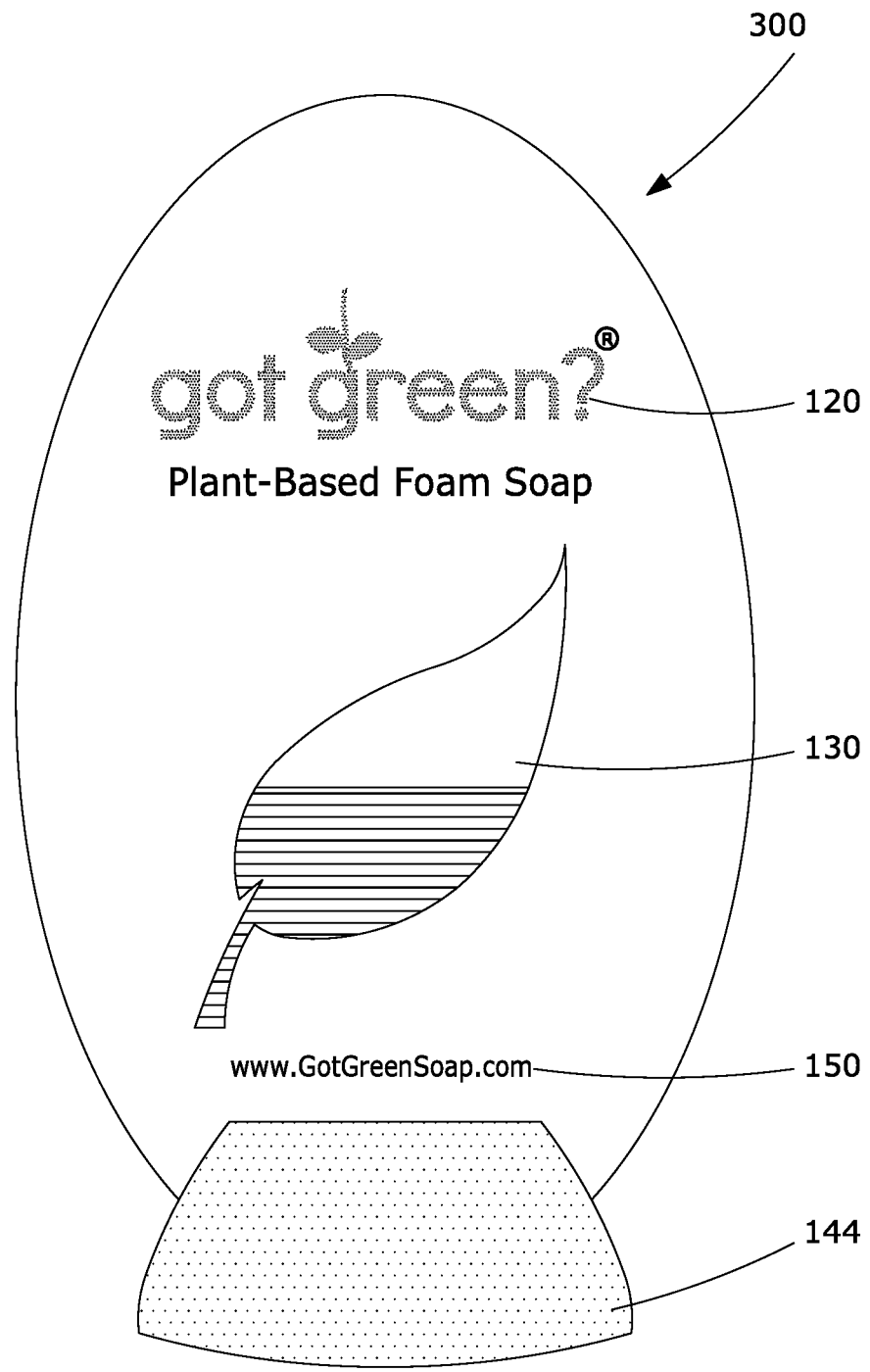
FIG. 5 is a front elevation view of another exemplary manual foaming soap dispenser of the present disclosure.
Figure 6:
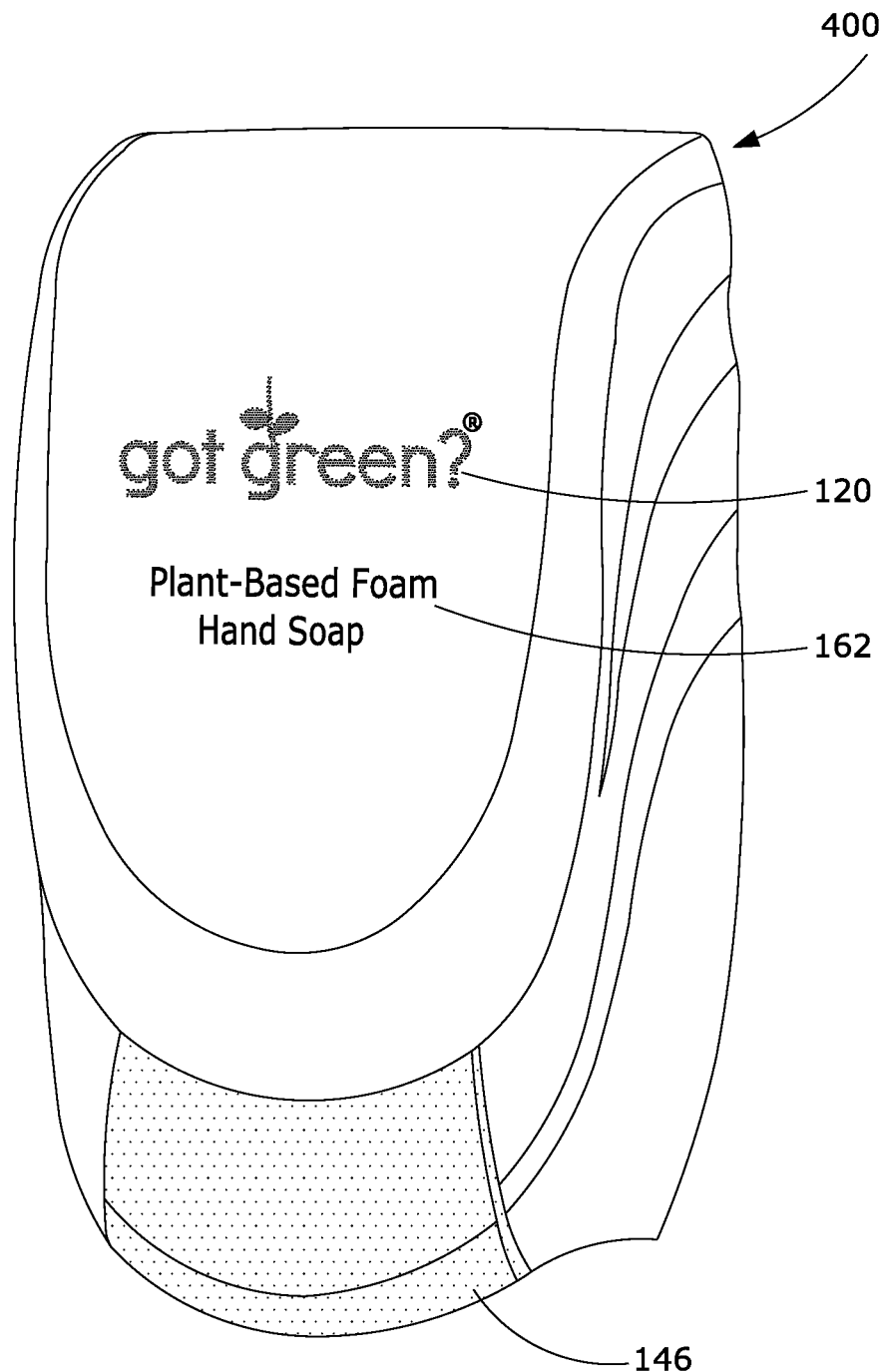
FIG. 6 is a front perspective view of a prior art manual foaming soap dispenser comprising the organic composition markings of the present disclosure.
Figure 7:
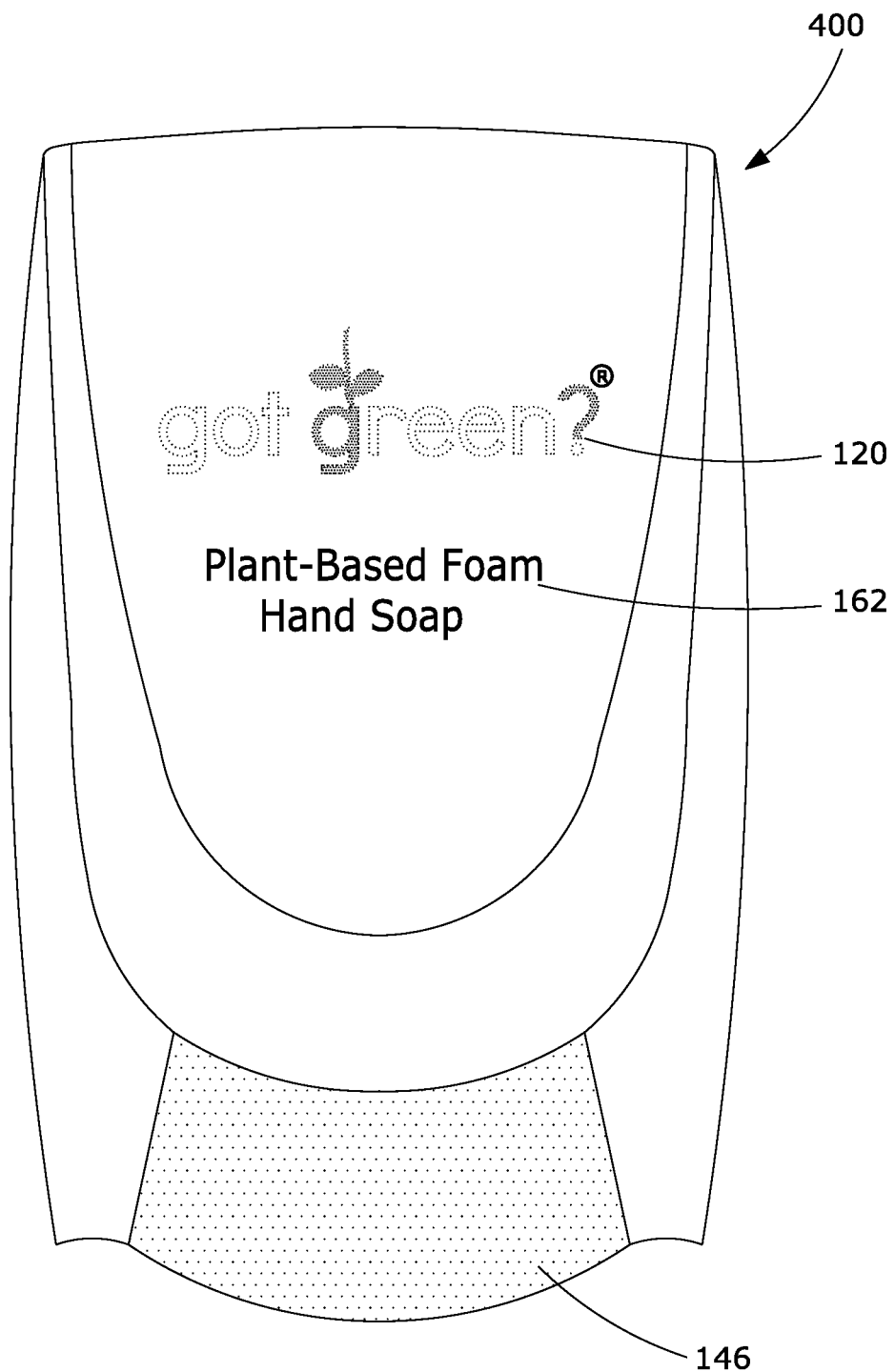
FIG. 7 is a front elevational view of the soap dispenser of FIG. 6.
Figure 8:
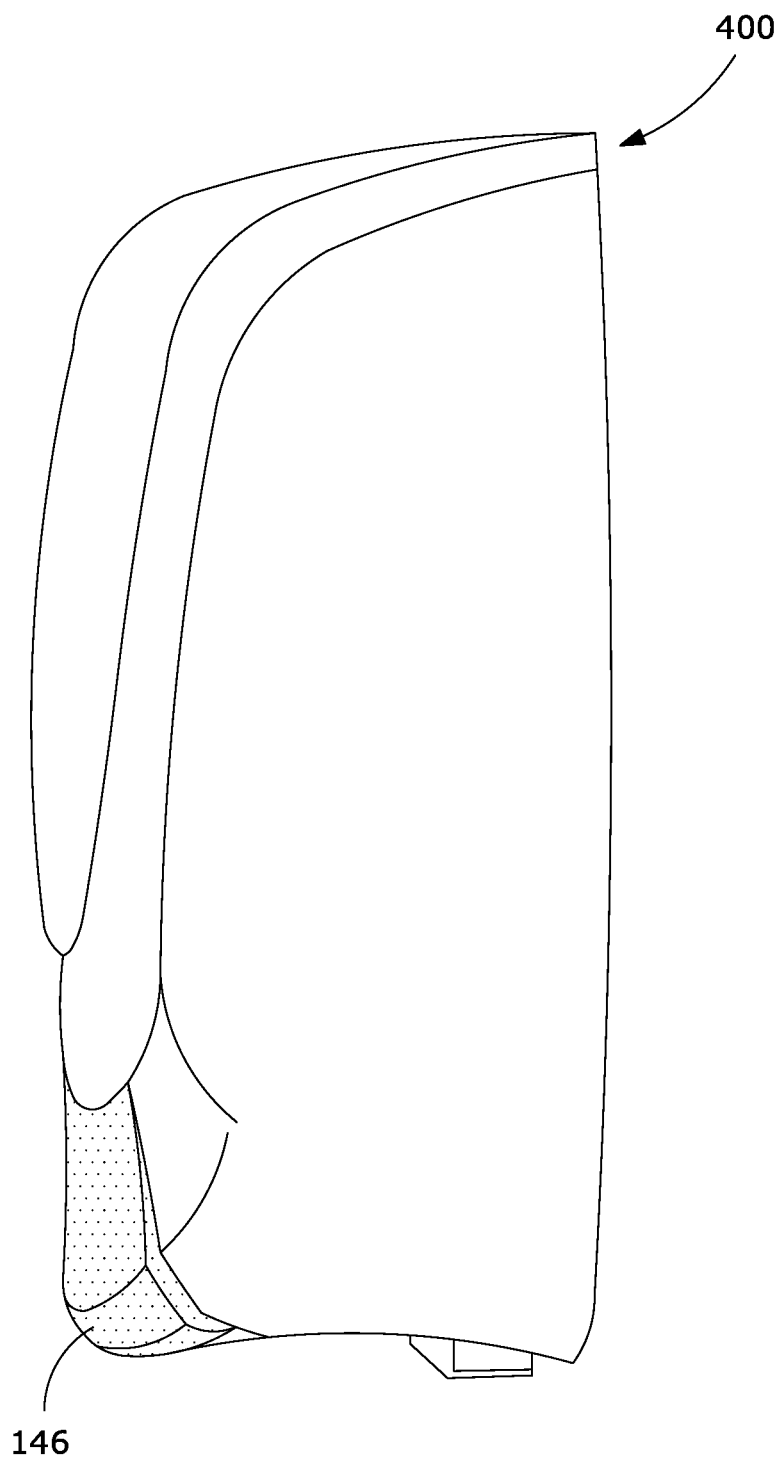
FIG. 8 is a right-side view of the soap dispenser of FIG. 6.
Figure 9:
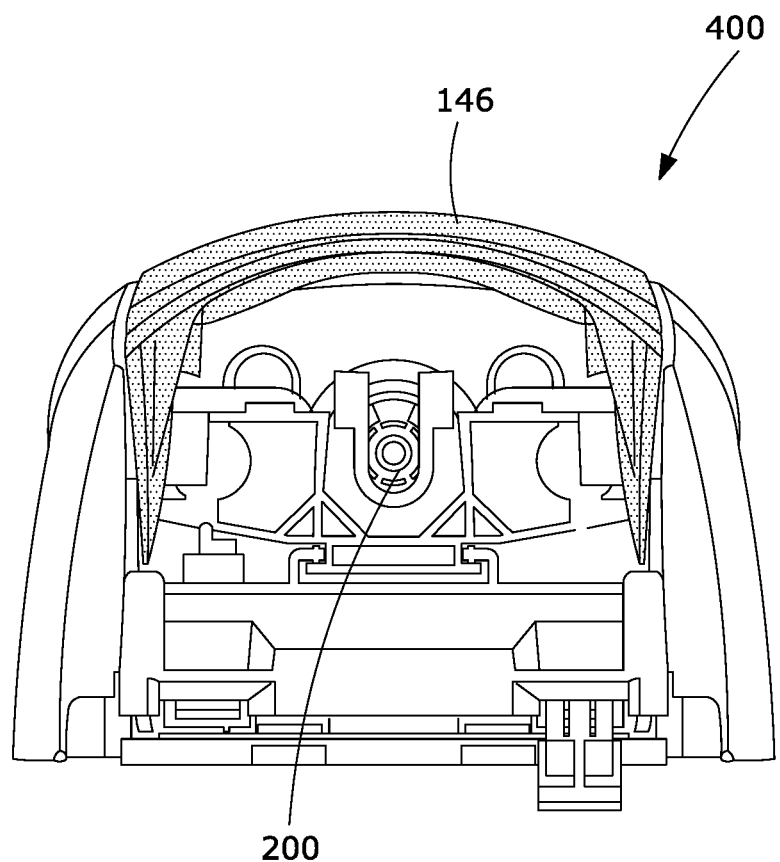
FIG. 9 is a bottom view of the soap dispenser of FIG. 6 that illustrates the foam dispensing nozzle.

As illustrated in FIGS. 3-5, the soap dispenser markings may further comprise a green, or partially green, colored leaf 130 on the front of the dispenser to indicate that the soap is plant-based.

Figure 10:
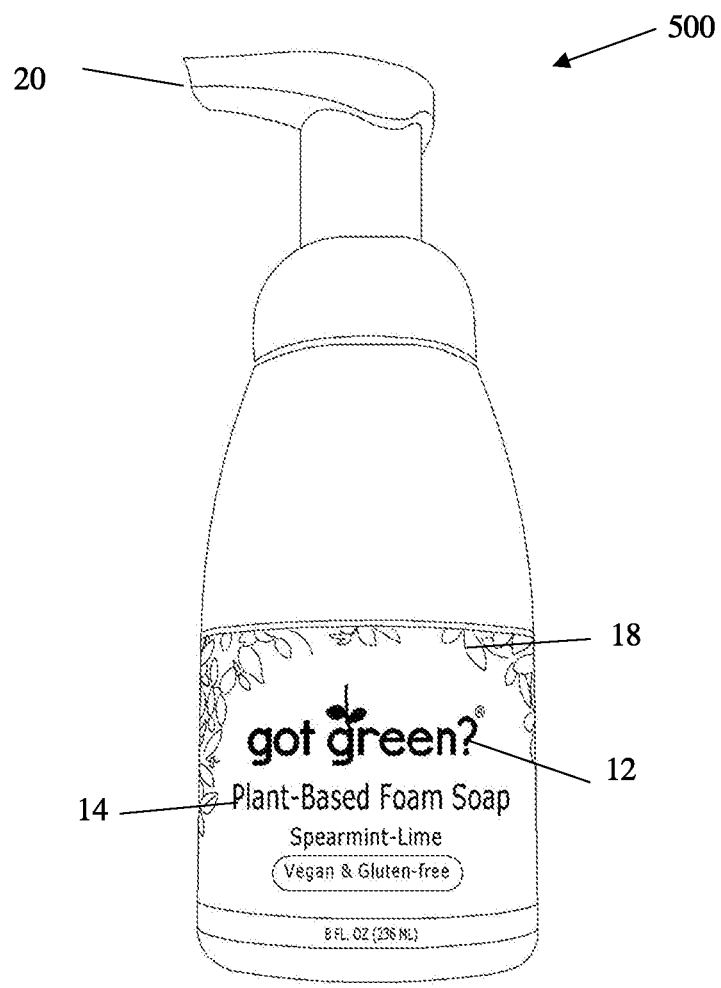
FIG. 10 is a front elevational view of an exemplary manual foaming soap dispenser of the present disclosure for use at a kitchen and bathroom sink and shower.
Figure 11:
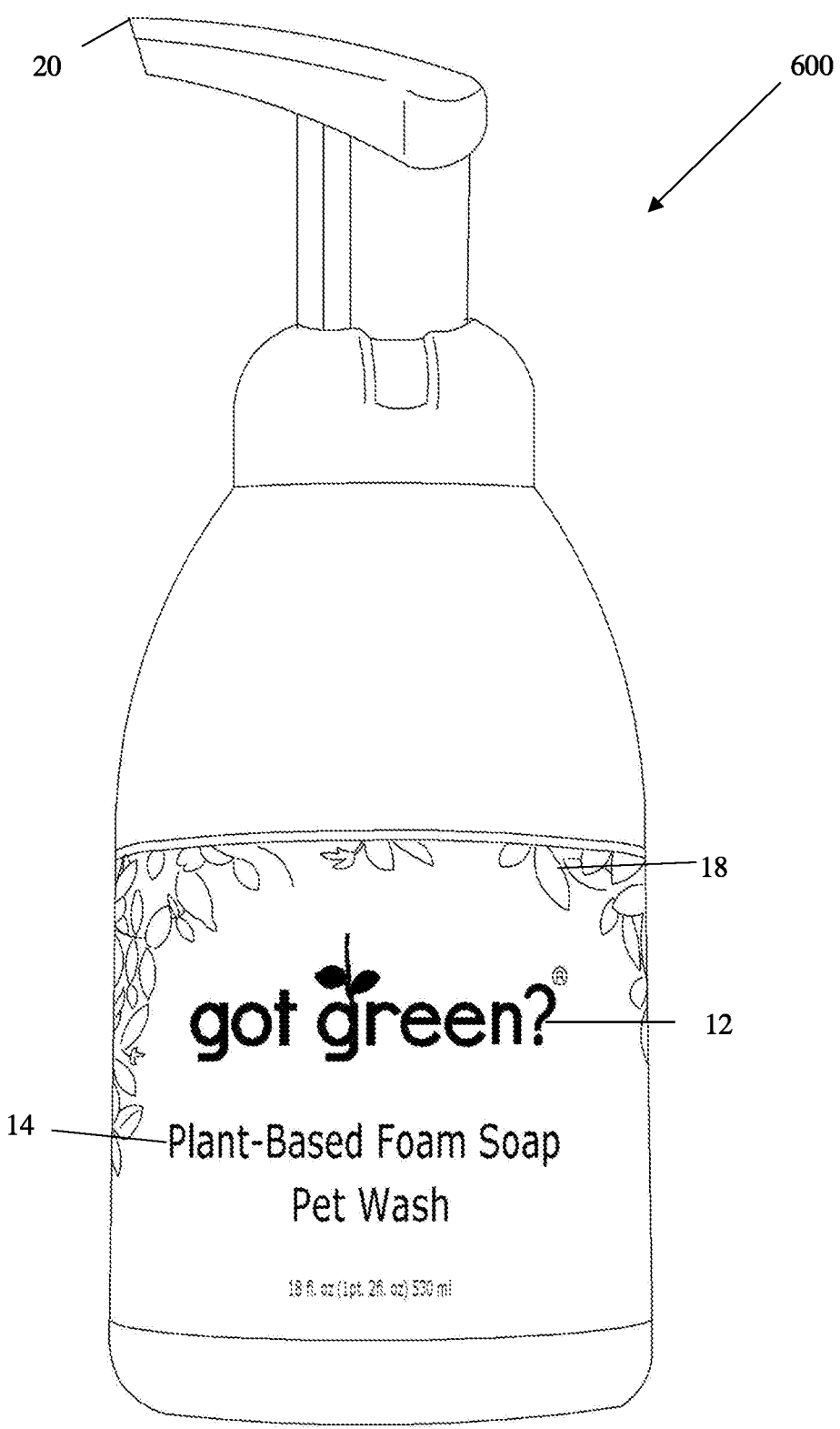
FIG. 11 is a front elevation view of an exemplary manual foaming soap dispenser of the present disclosure for use as a pet wash.
Figure 12:
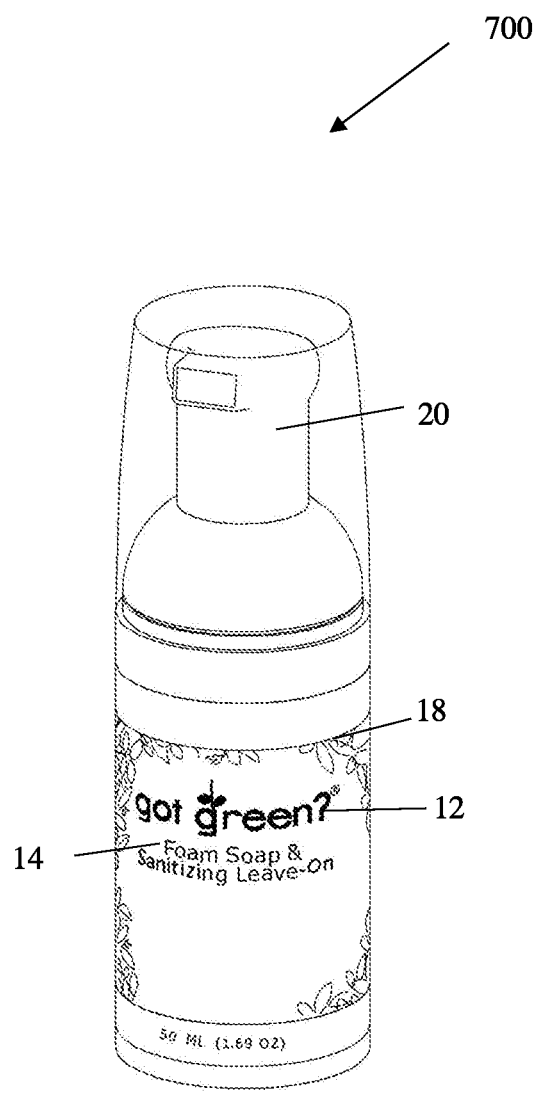
FIG. 12 is a front elevation view of another exemplary portable manual mini foaming soap dispenser of the present disclosure for a user to carry with them to clean and leave-on as an antimicrobial moisturizing sanitizer.

As illustrated in FIGS. 10-12, the dispensers of the present invention are portable manual pump down bottles of varying sizes. The push down pump 20 may dispense a liquid soap, or a foaming soap if the pump comprises a mechanism to force air into the liquid soap. For example, FIG. 10 is a portable foaming body soap dispenser 10 of 8 fluid ounces, e.g. for use on a bathroom sink or in a shower. FIG. 11 is a portable foaming pet body wash bottle 10 of 18 fluid ounces. FIG. 12 is a 1.69 fluid ounces mini-soap dispenser 10 for carrying with a user (e.g. backpack, purse, pants pocket, car, etc.). It is within the skill level of the artisan to construct a similar portable foaming soap dispenser sized for a specific purpose while storing the composition of the present invention, (e.g. 16-32 ounces or 30-50 milliliters for a shower or pet body wash).

As illustrated in FIGS. 10-12, the soap dispenser markings may further comprise a plurality of green colored leaves 18 on the front and/or back of the dispenser to indicate that the soap is plant-based.

Recyclable Dispenser: And in an embodiment, the entire dispenser, and the refillable or replaceable soap cartridge that it houses, are made entirely of recyclable plastic material, such polyethylene terephthalate (PET); high density polyethylene (HDPE); polyvinyl chloride; low density polyethylene (LDPE); polypropylene (PP); polystyrene (PS); ABS; and polyurethane.

Liquid Versus Foam Soap Dispensers

The soap compositions for the present disclosure are also housed in a soap dispenser that pumps out the soap in a liquid form, or as a foam, based upon the mechanical components of the dispenser. Foaming soap dispensers that mix the liquid soap with a gas, such as air or ozone, before dispensing are well known in the art, such as for air U.S. Pat. Nos. 6,409,050 B1; 8,091,739 B2; 8,113,388 B2; and 8,413, 852 B2, to Ophardt et al.; and for ozone see US Patent Application 20130119083 A1 to Ophardt et al.

In an embodiment, as disclosed in U.S. Pat. No. 6,409,050 B1 to Ophardt et al., a pump assembly provides for direct replacement of volumes of the organic liquid soap from a reservoir with equal volumes of air preferably at substantially atmospheric pressure. A slide arrangement preferably positively displaces liquid from the soap reservoir and air into the soap reservoir. The pump draws air from the atmosphere into a chamber from which the air either is available for passage to replace liquid from the reservoir, or is pressurized to assist dispensing liquid soap, preferably, admixing with the liquid to provide foaming soap. Gravity separation of air and liquid to be dispensed is used to replace liquid with air in the reservoir and to selectively place air and liquid into communication with passageways for ejection.

In another embodiment, the soap dispenser is an over-the-counter, portable product comprising a collapsible housing made from a recyclable plastic that contains from about 12 to about 56 fluid ounces of the organic soap composition of the present disclosure. A push down pump action handle enables the user to push down to receive a unit of liquid or foaming organic soap with each pump. For a body or pet wash, each pump should release a sufficient amount of the composition of the present invention to cover a reasonable area of a pet or human body part so that the user does not need to repeatedly pump out the composition to cover the entire body.

In an embodiment, as illustrated in FIGS. 3-9, the soap dispenser comprises a rigid housing that is wall-mounted, in a substantially oval shaped (e.g. FIG. 5), or a substantially rectangular shape (FIGS. 3, 4, 6-8). In an embodiment, the rectangular-shaped embodiment dimensions comprise: 263 mm in height, 159 mm in width, and 101 mm in depth-thickness.

The dispenser further comprises a recyclable dispenser refill container holding the soap composition of the present disclosure. In an embodiment, the refill container is shaped to be about: 8.5 inches in height, 5.5 inches in width, and 3 inches in depth, and holds about 1000 mL of the soap composition, e.g. as per Table 1.

In another embodiment, the soap dispenser comprises a rigid housing that is affixed to, or within the sink, and adjacent to the faucet (e.g. see U.S. Pat. No. 8,991,657 to Ciavarella et al., and US Patent Application 20170027390 A1 to Maercovich, wherein the entire contents of both are incorporated by reference in its entirety).

Manual Soap Dispensers

Manual Activated Dispensers are well known in the art, and for use in the present disclosure generally comprise internal components and mechanisms comprising: a manually top operable pumping means; and a liquid soap filled reservoir that is operatively connected to the pumping means for supplying soap to be dispensed with air to make a foaming soap. In an embodiment, the dispenser further comprises a vertically mounted tube extending between the reservoir and a dispenser nozzle with a close/open valve to let air enter the pump.

Exemplary manual activated dispensers for use with the bottle housings of FIGS. 3-5 for dispensing premeasured amounts of the liquid or foam organic soap composition of the present disclosure comprise, for example, U.S. Pat. No. 6,086,162 to De Winter et al.; U.S. Pat. Nos. 6,409,050 B1; 8,091,739 B2; 8,113,388 B2; and 8,413,852 B2, to Ophardt et al.

Body Wash for Humans

The compositions of the present invention can be used as a human body wash, such as in a shower, to clean, moisturize and hydrate a user's entire surface skin on their body. Other benefits for using the compositions disclosed herein comprise one or more of the following. The composition is: anti-acne on the face and body to prevent and treat acne by reducing the bacteria on the skin that causes it (11); and, anti-aging, primarily due to the thymol & rosemary that helps to preserve the skin and ward off pre-mature aging. When the composition of the present invention is used as a leave-on sanitizer or conditioner, it reduces the appearance of fine lines on the user's skin surface (12). When used as body wash or bubble bath, also prevents mold from growing in the tub and drain.

The composition is also good for preventing facial hair growth in woman due to the spearmint oil that has been proven to reduce growth of unwanted facial hair caused by elevated hormone levels (13); and it is good for cellular healing in pre-cancerous or skin cancer cells (14).

The composition also removes and helps to heal eczema and other skin afflictions from the surface of the skin. It is also highly moisturizing body wash by preventing and washing away bacterial build-up on the skin's surface before and after workouts; and the shea butter and other base ingredients are used as emollients, boosting the skin's hydration and also contains anti-inflammatory properties.

The composition also helps to remove and prevent parasitic infection with the composition's oil blend. And it helps to prevent and treat tinea (e.g. ringworm, athlete's foot and jock itch) on the body skin surface by using an antimicrobial ingredients that kill or slow the spread of microorganisms which include bacteria, viruses, protozoan and fungi such as mold and mildew (15, 16, 17). And it has been shown to prevent athlete's foot in an experiment in which after several days of applying as a "leave-on" wash and after cleaning the infected area, there was almost a 100% improvement in the infection. It is also effective for treating skin rashes and calming all inflammatory skin conditions (18).

It has also been tested at the Lymphedema Alliance of New York for being used as a leave-on product before a patient that is wrapped. Composition was shown to reduce inflammation, swelling, and bacteria from the moisture, etc.

It can also be used as a bubble bath or soak for many holistic purposes to calm the body and mind. Thymol reduces oxidative stress.

In the present invention, the hand soap is in a portable dispenser of about 8 to about 12 fluid ounces, per FIG. 10; and the mini-foamer of FIG. 12 is in a container of about 30 to about 50 milliliters (or 1-3 fluid ounces). The soap is also stored and shipped in a refill container (e.g. a milk jug style) for about 32 to about 128 fluid ounces.

Pet Wash:

The compositions of the present invention can also be used as a pet wash, such as bath to clean the pet's fur, especially when the pet is a mammal. The composition can also be used to wash pet toys and food dishes to remove built-on residue and reduce bacteria on the object's surfaces. Other benefits for using the compositions disclosed herein as a pet wash (e.g. dogs and cats) comprise one or more of the following: to soften the pet's fur coat, while keeping it very healthy (22); is chemical free, therefore reducing the pet's allergies, this then reduces the amount of pet hair that is shed (19); prevents tick and fleas and can be used as a wash for flea baths. A smaller amount can be left on the pet's fur coat as a non-toxic bug repellent (20). The wash can also help prevent parasitic skin afflictions. Tiny parasitic mites can burrow into the pet's skin. The composition helps to prevent this, as the odor of essential oils acts as a repellant to many bugs.

The composition as a pet wash is able to wash away impurities on the surface of the coat, while also reducing bacteria, and treating dry skin, impetigo, dermatitis, folliculitis and dandruff (21).

The composition can work in aromatherapy. The essential oils in the composition are therapeutic and healing for the animal by reducing the stress levels in animals, especially those with PTSD. The composition's thymol has powerful, proven, anti-anxiety effects and is able to soothe and calm the pet, while providing anti-bacterial and anti-itch properties (23).

The composition is non-toxic to animals. Flea control chemicals can build up in a pet's system and cause health problems. Flea sprays and dips that contain "all natural Pyrethrin" can be toxic to some pets, and Pyrethroids, synthetic derivatives of pyrethrins, expose your pet to more chemicals (24). The compositions of the present invention do not contain pyrethrin or other toxic synthetic chemicals.

CONCLUSION

As used herein, "substantially" refers to possible relatively small deviations (if any) of the stated shape. Other features that are considered as characteristic for the various embodiments are set forth in the appended claims. As used herein, the term "about" refers to The term "about" as used herein refers to a value within 10% of the underlying parameter (i.e., plus or minus 5%), and use of the term "about" at the beginning of a string of values modifies each of the values (i.e., "about 1, 2 and 3" refers to about 1, about 2 and about 3). Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

The transitional term "comprising", which is synonymous with "including," "containing," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Or, the technology illustratively described herein suitably may be practiced in the absence of any element(s) not specifically disclosed herein. Thus, for example, in each instance herein any of the terms "comprising," "consisting essentially of," and "consisting or" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed.

Although the various embodiments are illustrated and described herein as embodied in organic soap compositions and dispensers, it is nevertheless not intended to be limited to the details shown, since various modifications and structural changes may be made therein without departing from the spirit of the invention and within the scope and range of equivalents of the claims.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order and are not meant to be limited to the specific order or hierarchy presented.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as an "aspect" may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such an "embodiment" may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as a "configuration" may refer to one or more configurations and vice versa.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology.

LIST OF REFERENCES CITED

1) Genena A K; Hense H; Junior A S; de Souza S M. "Rosemary (*Rosmarinus officinalis*)—a study of the composition, antioxidant and antimicrobial activities of extracts obtained with supercritical carbon dioxide," Food Science and Technology, April/June 2008; 28(2): 463-469.
2) Al-Hijazeen M, Al-Rawashdehi M. "Preservative effects of rosemary extract (*Rosmarinus officinalis* L.) on quality and storage stability of chicken meat patties," Food Sci. Technol, ahead of print Epub Nov. 13, 2017.
3) Shahbazi Y. "Chemical Composition and In Vitro Antibacterial Activity of *Mentha spicata* Essential Oil against Common Food-Borne Pathogenic Bacteria," J Pathog. 2015; 1-5.
4) Shahbazi Y, Karami N, Shavisi N. "Effect of *Mentha spicata* essential oil on chemical, microbial, and sensory properties of minced camel meat during refrigerated storage," February 2018; 38(1): 1-7.
5) Sowndhararajan K, Kim S. "Influence of Fragrances on Human Psychophysiological Activity: With Special Reference to Human Electroencephalographic Response," Sci Pharm. 2016; 84(4): 724-752.
6) Bhandari S S, Kabrab M P. "To evaluate anti-anxiety activity of thymol," Journal of Acute Disease. 2014, 3(2): 136-140.
7) Priestley C M, Williamson E M, Wafford K A, and Sattelle D B. "Thymol, a constituent of thyme essential oil, is a positive allosteric modulator of human GABA receptors and a homo-oligomeric GABA receptor from *Drosophila melanogaster*," Br J Pharmacol. 2003 December; 140(8): 1363-1372.
8) Lockette T. "Florida researchers use essential oil as earth-friendly pesticide," SouthEast FarmPress, Apr. 21, 2004.
9) EPA Red Facts, Thymol, EPA-738-F-93-010, September 1993.
10) T M Nalawade, K Bhat, SHP Sogi, "Bactericidal activity of propylene glycol, glycerine, polyethylene glycol 400, and polyethylene glycol 1000 against selected microorganisms," J Int Soc Prev Community Dent. 2015 March-April; 5(2): 114-119.
11) M. H. Taleb et al., "*Origanum vulgare* L. Essential Oil as a Potential Anti-Acne Topical Nanoemulsion—In Vitro and In Vivo Study", Molecules. 2018 September; 23(9): 2164.
12) T. H. Lee et al., "Protective effect of Thymol essential oil from Thynus quinquecostatus extracts on U V irradiation-induced skin aging by supressing MMP-1 expression and collagen degradation", Federation of American Societies for Experimental Biology (FASEB), Abstract, Vol. 32, Issue S1, 1 Apr. 2018.
13) "Tea 'controls female hair growth'", BBC News Online, 20 Feb. 2007.
14) M. T. Islam et al., "Anticancer Activity of Thymol: A Literature Based Review and Docking Study with Emphasis on its Anticancer Mechanisms", IUBMB Life, 11 Oct. 2018, pages 9-19.
15) El-Shoraky and Shala, "Antifungal Activity of Spearmint and Peppermint Essential Oils against *Macrophomina* Root Rot of Cotton", J. Plant Prot. and Path., Mansoura Univ., Vol. 9 (11): 775-781, 2018.
16) Alves et al., "Unveiling the Antifungal Potential of Two Iberian Thyme Essential Oils: Effect on *C. albicans* Germ Tube and Preformed Biofilms", Front Pharmacol. 2019; 10: 446.
17) L. Jing et al., "Antifungal Activity of Citrus Essential Oils", Journal of Agricultural and Food Chemistry, March 2014, Abstract.
18) P. Mollarafie et al., "Antibacterial and wound healing properties of thymol (*Thymus vulgaris* Oil) and its application in a novel wound dressing", Journal of Medicinal Plants, December 2015, 14(53):69-81, Abstract.
19) K. Alt, "Doggy Day Spa: Essential Oils for Dogs", Canine Journal Online, Oct. 18, 2019.
20) P. Junquera, "THYMOL, Natural Plant Insecticide for veterinary use in DOGS, CATS, HORSES, CATTLE, SHEEP, GOATS, PIGS & POULTRY", Nov. 19, 2018.
21) "Best Antibacterial Dog Shampoos Medicated, Natural & Spray", Reviews Worthy. Aug. 29, 2020.
22) Grieves, "Natural Oils for Dogs That Can Help With Dog Skin Conditions", Pet MD, Dec. 11, 2018.
23) S. S. Bhandari et al., "To evaluate anti-anxiety activity of thymol", Journal of Acute Disease, Volume 3, Issue 2, 2014, Pages 136-140, Abstract.
24) G. Seaman, "8 Common Household Chemicals Harming your Pets, & their Non-Toxic Alternatives", Mar. 16, 2012.

OTHER CITED REFERENCES

U.S. Pat. No. 6,409,050 B1 that issued Jun. 25, 2002 to Ophardt et al.
U.S. Pat. No. 8,091,739 B2 that issued Jan. 10, 2012 to Ophardt et al.
U.S. Pat. No. 8,113,388 B2 that issued Feb. 14, 2012 to Ophardt et al.
U.S. Pat. No. 8,413,852 B2 that issued May 16, 2013 to Ophardt et al.
U.S. Pat. No. 8,308,027 B2 that issued Nov. 13, 2012 to Law et al.
U.S. Pat. No. 6,390,329 B1 that issued May 21, 2002 to J. T. Maddox.
U.S. Pat. No. 7,281,643 B2 that issued Oct. 16, 2007 to P H Lin.
U.S. Pat. No. 5,492,247 that issued Feb. 20, 1996 to Shu et al.
U.S. Pat. No. 8,991,657 that issued Mar. 31, 2015 to Ciavarella et al.
U.S. Pat. No. 6,068,162 that issued May 30, 2000 to De Winter et al.
US Patent Application 20130119083 A1 that issued May 16, 2013 to Ophardt et al.
US Patent Application 20170027390 A1 that issued Feb. 2, 2017 to Maercovich.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the scope of the appended claims.

What is claimed is:

1. A foam producing plant-based moisturizing anti-microbial hand, body and pet wash composition product comprising:
   a) a foam-able organic, plant-based liquid moisturizing antibacterial body and pet wash composition comprising:
      a base wash, comprising:
         saponified organic coconut oil of about 50.0 wt. % to about 79.60 wt. %;
         saponified organic olive oil of about 1.0 wt. % to about 3.40 wt. %;
         saponified organic sunflower oil of about 1.0 wt. % to about 5.0 wt. %;
         saponified organic jojoba oil of about 0.20 wt. % to about 3.0 wt. %;
         organic aloe vera of about 0.001 wt. % to about 0.20 wt. %;
         glycerin of about 1 wt. % to about 5 wt. %;
         wherein said base wash comprises at least about 70 wt. % of the composition;
      a plurality of anti-microbial active ingredients comprising:
         organic shea butter;
         USDA approved spearmint oil;
         USDA approved lime oil;
         organic thyme oil; and
         organic rosemary extract;
   b) a portable or fixed foaming wash dispenser for dispensing the organic liquid wash composition as a premeasured amount of foaming hand, body and pet wash; and
   c) wherein the composition is able to eradicate about 74.6% through 77.6% of the bacterial strain *Staphylococcus aureus* after at least one minute of direct contact with the composition.

2. The organic plant-based moisturizing anti-microbial wash composition product of claim 1, wherein the organic shea butter is in a range from about 0.50 weight percent to about 5.0 weight percent.

3. The organic plant-based moisturizing anti-microbial wash composition product of claim 1, wherein the natural spearmint oil is in a range from about 0.50 weight percent to about 5.0 weight percent, and is USDA approved.

4. The organic plant-based moisturizing anti-microbial wash composition product of claim 1, wherein the natural lime oil is in a range from about 0.40 weight % to about 5.0 weight %, and is USDA approved.

5. The organic plant-based moisturizing anti-microbial wash composition product of claim 1, wherein the organic thyme oil is in a range from about 0.04 weight % to about 2.0 weight %.

6. The organic plant-based moisturizing anti-microbial wash composition product of claim 1, wherein the organic rosemary extract is in a range from about 0.01 weight % to about 0.13 weight %.

7. The organic plant-based moisturizing anti-microbial wash composition product of claim 1, wherein the foam wash dispenser is a portable or fixed manual wash dispenser comprising a manually operable pumping means that mixes air with a liquid wash within the dispenser to produce a foaming wash, with a dispenser able to hold a wash composition volume of 1-18 fluid ounces or about 30-50 milliliters.

8. The organic plant-based moisturizing anti-microbial wash composition product of claim 7, wherein the dispenser is a mini-bottle comprising about 1 to about 3 fluid ounces or about 30 to about 50 milliliters, of the composition and is able to be used as a leave on sanitizer.

9. The organic plant-based moisturizing anti-microbial wash composition product of claim 1, wherein the dispenser is a refill container comprising about 32 to about 128 fluid ounces.

10. The organic plant-based moisturizing anti-microbial wash composition product of claim 7, wherein the dispenser is a fixed wall mounted or a sink mounted dispenser.

11. A method of use of a foam producing moisturizing anti-microbial body and pet wash product comprising:
   a) providing
      a foam-able organic, plant-based liquid moisturizing antibacterial body and pet body wash composition comprising:
      a base wash, comprising:
         saponified organic coconut oil of about 50.0 wt. % to about 79.60 wt. %;
         saponified organic olive oil of about 1.0 wt. % to about 3.40 wt. %;
         saponified organic sunflower oil of about 1.0 wt. % to about 5.0 wt. %;
         saponified organic jojoba oil of about 0.20 wt. % to about 3.0 wt. %;
         organic aloe vera of about 0.001 wt. % to about 0.20 wt. %;
         glycerin of about 1 wt. % to about 5 wt. %;
         wherein said base wash comprises at least about 70 wt. % of the composition;
      a plurality of anti-microbial active ingredients comprising:
         organic shea butter;
         natural spearmint oil;
         natural lime oil;
         organic thyme oil; and
         organic rosemary extract;
      a portable manual foaming wash dispenser for dispensing the organic liquid wash composition as a pre-measured amount of foaming wash;
   b) manually pumping said wash composition from a portable or a fixed dispenser comprising a mechanism to pump air into and mix with the liquid wash to produce a foaming wash;
   c) smoothing the foaming wash over a human hand or body, or a pet fur or body while the user is bathing or showering, wherein said user is a mammal; and
   d) rinsing said foaming wash off using clean water or leaving on as a moisturizing sanitizer.

12. The method of use of the wash composition of claim 11, wherein the foam wash dispenser is a portable or a fixed manual wash dispenser or a refill container comprising a manually operable pumping means that mixes air with a liquid wash within the dispenser to produce a foaming wash, with a dispenser able to hold a wash composition volume of about 1 to about 128 fluid ounces.

13. The method of use of the wash composition of claim 11, wherein the organic shea butter is in a range from about 0.50 weight percent to about 5.0 weight percent.

14. The method of use of the wash composition of claim 11, wherein the dispenser is a fixed as a wall mounted or a sink mounted dispenser.

15. The method of use of the wash composition of claim 11, wherein the organic wash composition further comprises at least one organic essential scented oil, or any combination thereof: orange essential oil, lemon essential oil, lime essential oil, citrus blend essential oil, kiwi oil, strawberry essential oil, raspberry essential oil, elderberry essential oil, juniper berry essential oil, cranberry essential oil, pomegranate essential oil, vanilla essential oil, lemongrass essential oil, rosemary essential oil, patchouli essential oil, thyme essential oil, spearmint essential oil, peppermint essential oil, wintergreen essential oil, cinnamon bark and leaf essential oil, sage essential oil, basil essential oil, sweet basil essential oil, pine blend essential oil, frankincense essential oil, ginger essential oil, mandarin essential oil, tangerine essential oil, grapefruit essential oil, floral fragrance, lavender essential oil, rose essential oil, *gardenia* essential oil, geranium essential oil, sweet marjoram oil, nutmeg essential oil, bergamot essential oil, cardamom essential oil, chocolate fragrance oil, and coconut fragrance oil.

16. The method of use of the wash composition of claim 15, wherein the natural spearmint oil is in a range from about 0.50 weight percent to about 5.0 weight percent, and is USDA approved.

17. The method of use of the wash composition of claim 15, wherein the natural lime oil is in a range from about 0.40 weight % to about 5.0 weight %, and is USDA approved.

18. The method of use of the wash composition of claim 15, wherein the organic thyme oil is in a range from about 0.04 weight % to about 2.0 weight %.

19. The method of use of the wash composition of claim 15, wherein the organic rosemary extract is in a range from about 0.01 weight % to about 0.13 weight %.

20. A soap composition comprising:
   a) a base soap comprising:
      a base wash, comprising:
         saponified organic coconut oil of about 50.0 wt. % to about 79.60 wt. %;
         saponified organic olive oil of about 1.0 wt. % to about 3.40 wt. %;
         saponified organic sunflower oil of about 1.0 wt. % to about 5.0 wt. %;
         saponified organic jojoba oil of about 0.20 wt. % to about 3.0 wt. %;
         organic aloe vera of about 0.001 wt. % to about 0.20 wt. %;
         glycerin of about 1.0 wt. % to about 5.0 wt. %;
         wherein said base wash comprises at least about 70.0 wt. % of the composition;
   b) a plurality of anti-microbial active ingredients comprising:
      organic shea butter;
      USDA approved spearmint oil;
      USDA approved lime oil;
      organic thyme oil; and
      organic rosemary extract;
   c) wherein the composition is able to eradicate about 74.6% through 77.6% of the bacterial strain *Staphylococcus aureus* after at least one minute of direct contact with the composition; and d) wherein said soap is useable to be used as a hand and body soap, and a pet wash, and a moisturizing leave on sanitizer.

* * * * *